United States Patent [19]

Ecker

[11] Patent Number: 5,512,438
[45] Date of Patent: Apr. 30, 1996

[54] INHIBITING RNA EXPRESSION BY FORMING A PSEUDO-HALF-KNOT RNA AT THE TARGET'S RNA SECONDARY STRUCTURE USING ANTISENSE OLIGONUCLEOTIDES

[75] Inventor: David Ecker, Leucadia, Calif.

[73] Assignee: ISIS Pharmaceuticals, Inc., Carlsbad, Ga.

[21] Appl. No.: 176,314

[22] Filed: Jan. 3, 1994

Related U.S. Application Data

[63] Continuation of Ser. No. 916,764, Jul. 20, 1992, abandoned.
[51] Int. Cl.[6] ............................ C07H 21/04; C12Q 1/68; C12Q 1/70
[52] U.S. Cl. ................... 435/6; 435/5; 536/24.5; 935/33
[58] Field of Search ..................... 435/6, 5; 536/24.5; 935/33; 514/44

[56] References Cited

U.S. PATENT DOCUMENTS

| 4,806,463 | 2/1989 | Goodchild et al. | 435/5 |
| 5,034,506 | 7/1991 | Summerton et al. | 528/391 |
| 5,220,014 | 6/1993 | Ackerman et al. | 526/24.5 |

FOREIGN PATENT DOCUMENTS

0386563A1  2/1990  European Pat. Off. .

OTHER PUBLICATIONS

Ecker et al. Science 257:958–961, 1992.
Chiang et al. J. Biol. Chem. 266(27):18162–18171 (1991).
Ratner, M. Bio/Technology 1:207, 1989.
Simons et al., Nature 359:67–70, 1992.
Breslauer et al, Predicting DNA duplex stability from the base sequence *Proc. Natl. Acad. Sci. U.S.A.* 83, 3746 (1986).
Casey et al., Iron-Responsive Elements: Regulatory RNA Sequences That Control mRNA Levels and Translation *Science* 240, 924 (1988).
Chen & Sigman, Sequence–Specific Scission of RNA by 1,10–Phenanthroline–Cooper Linked to Deoxyoligonucleotides *J. Am. Chem. Soc.* 110, 6570 (1992).
Dingwall et al., HIV–1 tat protein stimulates transcription by binding to a U–rich bulge in the stem of the TAR RNA structure *EMBO J.* 9, 4145 (1990).
Dingwall et al., Human immunodeficiency virus 1 tat protein binds trans–activation–responsive region (TAR) RNA in vitro *Proc. Natl. Acad. Sci. USA* 86, 6925 (1989).
Eguchi et al., Antisense RNA[1] *Annu. Rev. Biochem.* 60, 631 (1991).
Freier et al., Improved free–energy parameters for predictions of RNA duplex stability *Proc. Natl. Acad. Sci. U.S.A.* 83, 9373 (1986).
Freier et al., Thermodynamics of Antisense Oligonucleotide Hybridization *Gene Regulation by Antisense Nucelic Acids*, 95 (1991).
Heidenreich et al., Hammerhead Ribozyme–mediated Cleavage of the Long Terminal Repeat RNA of Human Immunodeficiency Virus Type 1 *J. Biol. Chem.* 267, 1904–1909 (1992).
Hsu et al., Inhibition of HIV Replication in Acute and Chronic Infections in Vitro by a Tat Antagonists *Science* 254, 1799 (1991).
Junker–Niepmann et al., A Short cis–acting sequence is required for hepatitis B virus pregenome encapsidation and sufficient for packaging of foreign RNA *EMBO J.* 9, 3385 (1990).

(List continued on next page.)

*Primary Examiner*—W. Gary Jones
*Assistant Examiner*—Paul B. Tran
*Attorney, Agent, or Firm*—Woodcock Washburn Kurtz MacKiewicz & Norris

[57] ABSTRACT

Compositions and methods for modulating the activity of RNA are provided. Oligonucleotides are hybridized with an RNA structure to form a stable heteroduplex so that the RNA is no longer recognized by its regulatory protein after oligonucleotide binding. Reactive moieties can be tethered to the oligonucleotide that enhance its activity. Antisense oligonucleotides directed against HIV TAR are provided.

9 Claims, 8 Drawing Sheets

OTHER PUBLICATIONS

McPheeters et al., Autogenous Regulatory Site on the Bacteriophase T4 Gene 32 Messenger RNA *J. Mol. Biol.* 201, 517 (1988).

Nielsen et al., Sequence–Selective Recognition of DNA by Strand Displacement with a Thymine–Substituted Polyamide *Science* 254, 1497 (1991).

Pleij, C. W., Pseudoknots: a new motif in the RNA game *TIBS* 15, 143 (1990).

Pleij & Bosch, RNA Pseudoknots: Structure, Detection, and Prediction *Methods. Enzymol.* 180, 289 (1989).

Pleij et al., A new principle of RNA folding based on pseudoknotting *Nucleic. Acids. Res.* 13, 1717 (1985).

Puglisi et al, RNA Pseudoknots *Accounts Chem. Res.* 24, 152 (1991).

Roy et al., A bulge structure in HIV–1 TAR RNA is required for Tat binding and Tat–mediated transactivation *Genes Dev.* 4, 1365 (1990).

Rosen & Pavlakis, Tat and Rev: positive regulators of HIV gene expression *AIDS* 4, 499 (1990).

Saenger, W., *Principles of Nucleic Acid Structure* (Springer–Verlag, New York, 1983).

Sigman, D. S., Nuclease Activity of 1,10–Phenanthroline–Copper Ion *Acc. Chem. Res.* 19, 180 (1986).

Sproat et al,, Highly efficient chemical synthesis of 2'O–methyloligoribonucleotides and tetrabiotinylated derivatives; *Nucleic. Acids. Res.* 17, 3373 (1989).

Vickers et al., Inhibition of HIV–LTR gene expression by oligonucleotides targeted to the TAR element *Nuc Acids Res* 19 (12):3359–3368 (1991).

Weeks et al., Fragments of the HIV–1 Tat Protein Specifically Bind TAR RNA *Science* 249, 1281 (1990).

Weislow et al,, New Soluble–Formazan Assay for HIV–1 Cytopathic Effects *J. Nat'l Cancer Inst.* 81:577 1989.

Wickstrom et al., Complementary Olignucleotide Probe of Vesicular Stomatitis Virus Matrix Protein mRNA Translation *Biophys. J.* 49, 15 (1986).

Witherell et al., Cooperative Binding of R17 Coat Protein to RNA *Biochemistry* 29, 11051 (1990).

Wyatt et al., RNA Folding: Pseudoknots, Loops and Bulges *BioEssays* 11:100 1989.

PSEUDO-HALF-KNOT
FORMED BY
OLIGO-RNA COMPLEX

RNA PSEUDOKNOT

PSEUDO-HALF-KNOT
FORMED BY
OLIGO-RNA COMPLEX

RNA PSEUDOKNOT

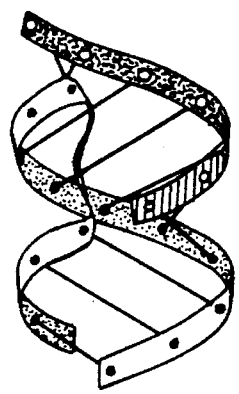 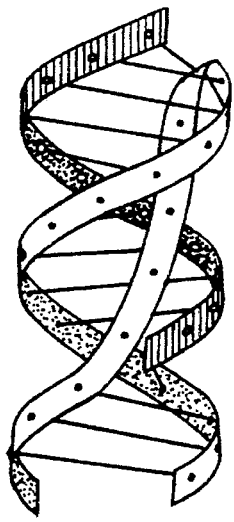 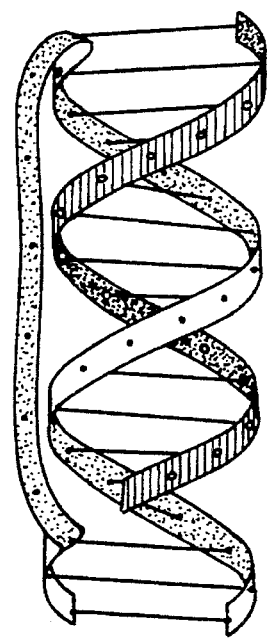
*Fig. 2A*   *Fig. 2B*   *Fig. 2C*

INHIBITING RNA EXPRESSION BY FORMING A PSEUDO-HALF-KNOT RNA AT THE TARGET'S RNA SECONDARY STRUCTURE USING ANTISENSE OLIGONUCLEOTIDES

This is a continuation, of application Ser. No. 07/916,764, filed Jul. 20, 1992 now abandoned.

FIELD OF THE INVENTION

This invention relates to compositions and methods for modulating the activity of RNA. Oligonucleotides are hybridized with RNA in accordance with novel motifs to effect modulation of RNA activity.

BACKGROUND OF THE INVENTION

Many investigators designing antisense oligonucleotides or ribozymes to inhibit specific RNA's generally avoid targeting regions with strong secondary structure to facilitate hybridization. E. Wickstrom, W. S. Simonet, K. Medlock, I. Ruiz-Robles, *Biophys. J.* 49, 15 (1986). However, structured RNA's generally contain single stranded portions which are available for base pairing; there may be thermodynamic, kinetic or functional advantages to targeting these regions. For example, natural antisense recognition systems in *E. coli* involve bimolecular interactions between two highly structured hairpin loops which have fast hybridization rates. Y. Eguchi, T. Itoh, J. Tomizawa, *Annu. Rev. Biochem.* 60, 631 (1991).

Specific regulatory proteins often recognize structured RNA regions such as the HIV TAR and RRE elements. C. Dingwall, I. Ernberg, M. J. Gait, et al, *Proc. Natl. Acad. Sci. USA* 86, 6925 (1989); C. Dingwall, I. Ernberg, M. J. Gait, et al, *EMBO J.* 9, 4145 (1990); S. Roy, U. Delling, C.-H. Chen, C. A. Rosen, N. Sonenberg, *Genes Dev.* 4, 1365 (1990); C. A. Rosen, G. N. Pavlakis, *AIDS* 4,499 (1990); K. M. Weeks, C. Ampe, S. C. Schultz, T. A. Steitz, D. M. Crothers, *Science* 249, 1281 (1990), the iron responsive element in mammalian cells, J. L. Casey, M. W. Hentze, D. M. Koeller, et al, *Science* 240, 924 (1988), and the R17 phage coat protein, G. W. Witherell, H.-N. Wu, O. C. Uhlenbeck, *Biochemistry* 29, 11051 (1990).

RNA viruses contain capsid proteins which specifically package only the viral genome by binding to structured RNA regions, M. Junker-Niepmann, R. Bartenschlager, H. Schaller, *EMBO J.* 9, 3389 (1990). Enhanced biological specificity can be obtained by targeting these regions. The cell will contain many non-targetRNA sequences to which the antisense compounds are either closely or precisely complementary. Although ribozymes bind and cleave their target RNA, other antisense molecules do not cleave their target and may not produce significant biological effects unless they compete effectively with a biomolecule for the target site. There are currently no reliable methods for determining accessible target sites.

In view of the potential advantages of binding to structured RNA's, compositions and methods for binding to structured regions are desired.

OBJECTS OF THE INVENTION

It is an object of the invention to provide compositions for modulating the activity of RNA, and methods for their design and fabrication.

It is a further object to provide methods for modulating the activity of RNA.

These and other objects will become apparent to persons of ordinary skill in the art from a review of the instant specification and appended claims.

SUMMARY OF THE INVENTION

Compositions and methods are provided for modulating the activity of RNA. An oligonucleotide is hybridized with selected RNA secondary structure so that the RNA is no longer recognized by its regulatory protein after oligonucleotide binding. The oligonucleotide and RNA structure are selected by analysis of target structure, complex stability and thermodynamics to allow design and optimization of functional antisense oligonucleotides. The oligonucleotide is hybridized to the RNA secondary structure, such as a hairpin loop, on either the 3' or 5' side of the loop, leaving some unpaired nucleotides to reach back to the original stem of the hairpin. Oligonucleotides of 7–25 nucleotide bases are preferred. Oligonucleotides having modifications of at least one of the 2'-deoxyfuranosyl moieties of the nucleoside unit are also preferred. Oligonucleotides having modified backbones are also preferred.

DESCRIPTION OF THE DRAWINGS

FIG. 1 (A) depicts an oligonucleotide binding to the 3' side of an RNA hairpin (Top Path) or 5' side (Bottom Path) yielding structures topologically similar to different halves of a pseudoknot with two coaxially stacked stems and a single loop which crosses the major groove (Top Path) or minor groove (Bottom Path). Ribbon drawings of L1(top) (B) and L2 (D) (bottom) pseudo-half-knots and similarly oriented pseudoknots (C and E) are also shown.

FIG. 2(A) shows that it is possible for one nucleotide to span the major groove of an A-type helix with minimal perturbation of the helix structure. As the target loop size increases, the loop length difference between Loop 1 versus Loop 2 motifs narrows. As shown in FIG. 2(B), as the loop length increases, Loop 1's, which are normally restricted to following the major groove, have the potential to flip out of the major groove and follow a shorter path outside of the helix, as shown in FIG. 2(C). FIG. 2(A) shows a Loop 1, 7-mer oligonucleotide targeted to an 8-base hairpin loop, leaving a 1-base pseudo-half-knot loop; FIG. 2(B) shows a Loop 1, 12-mer oligonucleotide targeted to a 17-base loop; FIG. 2(C) shows a Loop 1, 17-mer oligonucleotide targeted to a 23-base loop in a flipped-out geometry.

DETAILED DESCRIPTION OF INVENTION

Pseudo-half-knotting and drug design

Figure 1A:
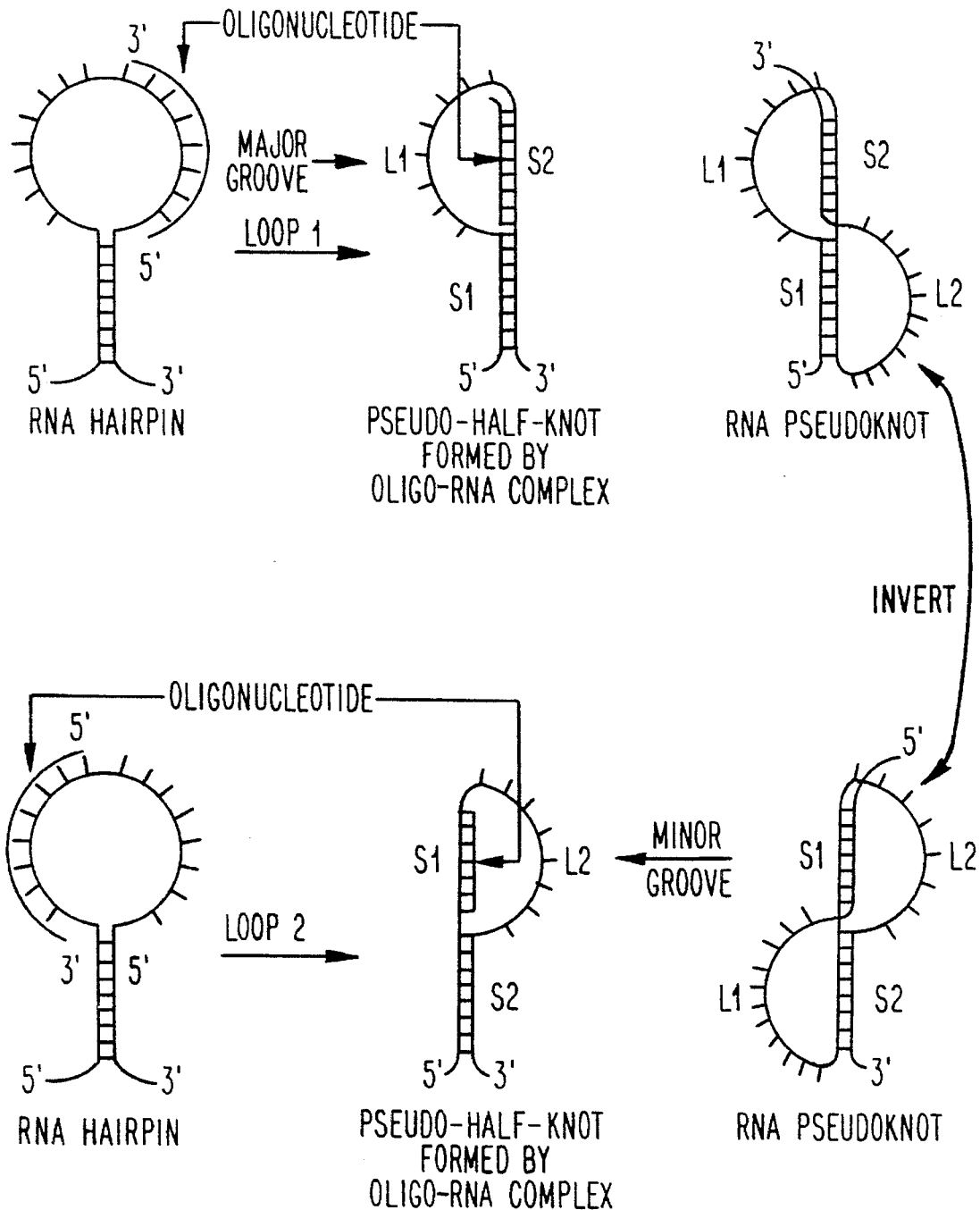
FIG. 1 comprising parts A–E shows the structure of a pseudo-half-knot. As shown, it is possible to bind on either the 5' or 3' sides of the loop of a hairpin structure leaving some unpaired nucleotides to reach back to the original stem; these two options produce different tertiary structures. The convention of pseudoknot nomenclature is to number the stems and loops as they first appear in the structure from 5' to 3'. Note that Loop 1 (L1) crosses stem 2 (S2) and Loop 2 (L2) crosses stem 1(S1). Although it is not apparent when depicted in two dimensions, L1 and L2 are topologically distinct; L1 crosses the major groove of RNA, while L2 crosses the minor groove.
Figure 1B:
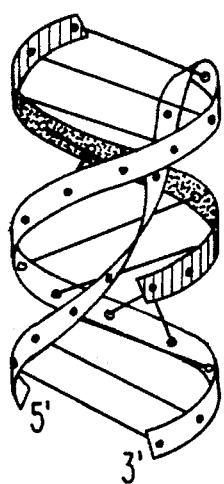
Figure 1C:
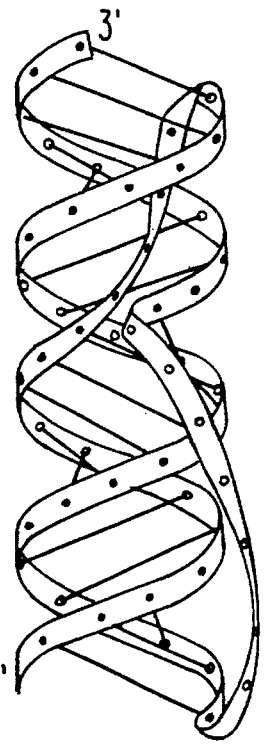
Figure 1D:
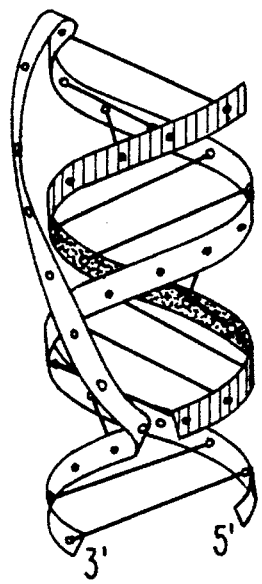
Figure 1E:
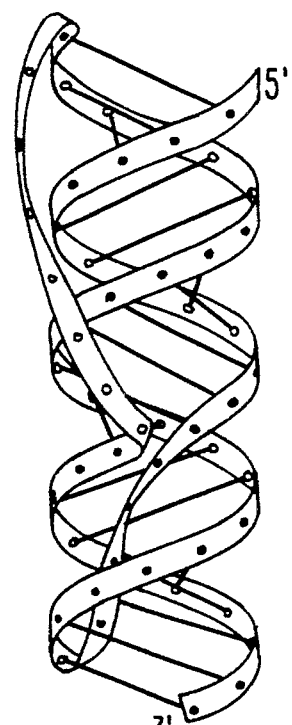

Considerable efforts are currently being directed at specifically targeting RNA for therapeutic purposes. Given an mRNA target sequence, complementary regions for antisense or ribozyme targeting can be selected. However, determining effective regions to target is more complex and there are currently no reliable methods for determining the accessible target sites on a given message. In one sense, all mRNA is structured. Computer RNA folding programs always predict a complex folded pattern for any long RNA, but extensive experimentation is required to determine which regions are truly accessible to binding. For example, it was reported that ribozymes targeted to three different regions of the HIV LTR RNA cleaved the target 1,000 fold less efficiently than corresponding short synthetic oligoribonucleotide substrates due to secondary structure in the RNA. O. Heidenreich, F. Eckstein, *J. Biol. Chem.* 267, 1904 (1992). By selecting short, relatively simple RNA structures, such as hairpin loops, increased reliability in predicting both the structure of the target before and after binding may be better realized.

Binding to structured RNA generally requires some disruption and replacement of existing base pairs and tertiary interactions with the new structure. Because the most important biological target sites may be structured, methods have been discovered to achieve the highest possible affinity for the target per unit length of oligonucleotide based upon theoretical and experimental results. Optimization begins with analysis of the structured target. Affinity is lost by breaking base pairs in the target RNA. Binding strategies should minimize the number of base pairs disrupted in the target structure by exploiting its weakest elements such as loop regions, short stems and bulged bases, which are thermodynamically destabilizing to the structure. In contrast, targeting long continuous stems which contribute to stabilizing the structure is avoided. Affinity is increased by maximizing the total number of binding interactions in the hybrid complex. This includes the base pairs between the oligonucleotide and target, new intramolecular base pairs in the rearranged target and tertiary interactions between the heteroduplex and intramolecular stems in the structure. Topological considerations are essential to maximize stem lengths in the complex and minimize loop lengths.

It has been found that the most stable heteroduplexes are formed by targeting sequences that maximize base stacking using the RNA near neighbor thermodynamic parameters. As seen in Table 1, $\Delta G°_{stem}$ is a major component to overall hybridization. In contrast to "linear" RNA, when targeting RNA secondary structure the number of base pairs that can productively be complemented is often limited. Therefore, the oligonucleotide type with the highest affinity per unit base should be used. The 2'-O-alkyl oligonucleotides are high affinity analogs. They are resistant to nucleolytic degradation and can be used in cell culture experiments, S. M. Freier, W. F. Lima, Y. S. Sanghvi et al., in *Gene Regulation by Antisense Nucleic Acids,* 1991. Backbone modified oligonucleotides in which there is a reduction in the negative charge also form stable structures when bound to RNA. Potential intramolecular structure in the oligonucleotide must also be considered ($\Delta G°_1$). The oligonucleotides should not have strong internal structure or form stable dimers. All bases in the oligomer should be paired to the target or involved in stabilizing tertiary interactions. Unpaired bases cause loss in specificity by increasing affinity at non-target sites. Moreover, longer oligonucleotides have greater potential for internal structure. Initiation of hybridization must occur at a single stranded, preferentially prestacked, region of the target RNA followed by zippering into more structured regions of the target. If the objective of RNA binding is to compete with a regulatory protein, the RNA should no longer be recognized by its regulatory protein after oligonucleotide binding.

There are important advantages in drug design to knowing the structure of the drug/target complex. In the present invention, a single stranded region of the target RNA is brought into close proximity with the oligonucleotide drug. Cleavage reagents that prefer single stranded RNA targets could be tethered to oligonucleotides at a variety of positions to achieve cleavage. In this way, a drug moiety could be attached to an oligonucleotide which interacts with the target.

Pseudo-half-knot binding to RNA

The simplest example of an RNA secondary structure is a hairpin consisting of a double stranded stem region and single stranded loop. Hybridization to all the unpaired bases in the loop would seem an attractive targeting strategy. However, hybridization to all the bases of a single stranded RNA hairpin loop while maintaining the base pairing in the stem is topologically impossible. Double strand hybrids are relatively stiff and cannot follow the same circular path as the more conformationally flexible single stranded RNA loops. Pseudoknots are nature's way of binding unpaired bases in hairpin loops in topologically stable structures. Pseudoknots are formed when the single stranded bases from the loop region of an RNA hairpin pair with bases adjacent to the hairpin forming a second stem and loop. C. W. A. Pleij, *TIBS* 15, 143 (1990); C. W. Pleij, L. Bosch, *Methods. Enzymol.* 180, 289 (1989); J. D. Puglisi, J. R. Wyatt, I. Tinoco, Jr., *Accounts Chem. Res.* 24, 152 (1991). The resulting structure consists of two stems stacked upon one another and two loops. See FIG. 1.

The invention mimics the binding patterns of naturally occurring pseudoknots. As in naturally occurring pseudoknots, it is possible to bind on either the 5' or 3' sides of the loop leaving some unpaired nucleotides to reach back to the original stem (FIG. 1). These two options, 5' side vs 3' side binding, produce significantly different tertiary structures.

The convention of pseudoknot nomenclature is to number the stems and loops as they first appear in the structure from 5' to the 3'. C. W. Pleij, K. Rietveld, L. Bosch, *Nucleic. Acids. Res.* 13, 1717 (1985). As shown in FIG. 1, Loop 1 (L1) crosses stem 2 (S2) and Loop 2 (L2) crosses stem 1 (S1). Although it is not apparent when depicted in two dimensions, L1 and L2 are topologically distinct; L1 crosses the major groove of RNA, while L2 crosses the minor groove. This significantly influences the number of bases required in each loop to cross a given length of stem. This relationship is complex; it is driven by the periodicity of the helix and the distance across each groove.

The present invention employs oligonucleotides hybridized to the loop of an RNA secondary structure. In the context of this invention, the term "oligonucleotide" refers to a polynucleotide formed from naturally occurring bases and pentofuranosyl groups joined by native phosphodiester bonds. This term effectively refers to naturally occurring species or synthetic species formed from naturally occurring subunits or their close homologs. The term "oligonucleotide" may also refer to moieties which function similarly to naturally occurring oligonucleotides but which have non-naturally occurring portions. Thus, oligonucleotides may have altered sugar moieties or inter-sugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the compositions or the ability of the compositions to penetrate into the region of cells where the RNA or DNA whose activity to be modulated is located. It is preferred that such substitutions comprise phosphorothioate bonds, phosphotriesters, methyl phosphonate bonds, short chain alkyl or cycloalkyl structures or short chain heteroatomic or heterocyclic structures. Most preferred are $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$— $CH_2$ and O—$N(CH_3)$—$CH_2$—$CH_2$ structures (where phosphodiester is O—P—O—$CH_2$). Also preferred are morpholino structures. For example, see U.S. Pat. No: 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 254, 1497 (1991).

In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group.

Such oligonucleotides are best described as being functionally interchangeable with natural oligonucleotides, or synthesized oligonucleotides along natural lines, but which have one or more differences from natural structure. All such oligonucleotides are comprehended by this invention so long as they function effectively to hybridize with the RNA. The oligonucleotides in accordance with this invention preferably comprise from about 5 to about 50 nucleic acid base units. It is more preferred that such oligonucleotides comprise from about 7 to 25 nucleic acid base units, and still more preferred to have from about 12 to 25 nucleotide units.

The oligonucleotides used in accordance with this invention may be conveniently and routinely made through the well-known technique of solid phase synthesis. Equipment for such synthesis is sold by several vendors including Applied Biosystems (Foster City, Calif.). Any other means for such synthesis may also be employed, however the actual synthesis of the oligonucleotides is well within the talents of the routineer. It is also well known to use similar techniques to prepare other oligonucleotides such as the phosphorothioates and alkylated derivatives.

When an antisense oligoribonucleotide is hybridized with the loop of a hairpin structure, the topology of the resulting complex resembles half of a pseudoknot and is denominated as a pseudo-half-knot. If hybridized to the 3' side of the loop, a structure equivalent to a pseudoknot stem 2 is formed and the looped-out RNA is equivalent to a pseudoknot Loop 1 (FIG. 1, top path). If hybridized to the 5' side of the loop, it forms a pseudo-half-knot stem 1 and the looped-out RNA is a Loop 2 (FIG. 1, bottom path). The bimolecular pseudo-half-knots can be defined by either the type of loop or stem formed. We arbitrarily choose to define pseudo-half-knots by the loop type; either Loop 1 (L1) or Loop 2 (L2) pseudo-half-knots.

As with natural RNA pseudoknots, the lengths of the stems and loops for the pseudo-half-knot are restricted by the constraints of the three dimensional structure. Because of the different distances across the major and minor grooves of the A-type helix, it is possible to have much shorter Loop 1's than Loop 2's. Pseudoknots have been reported with Loop 1's which consist of a single nucleotide, D. S. McPheeters, G. D. Stormo, L. Gold, *J. Mol. Biol.* 201, 517 (1988). Molecular modeling studies show that it is possible for one nucleotide to span the major groove of an A-type helix with minimal perturbation of the helix structure (FIG. 2A). As the target loop size increases, the loop length difference between Loop 1 vs Loop 2 motifs narrows. For loops of 17, it was found to be possible to hybridize to either the 3' or 5' side with a 12 base oligonucleotide and have 5 base loops due to the periodicity of the helix. As the loop length increased further, Loop 1's (FIG. 2B), which are normally restricted to following the major groove, have the potential to "flip-out" of the major groove and follow a shorter path outside the helix (FIG. 2C).

Binding to HIV TAR by pseudo-half-knotting

The HIV TAR element is an important RNA hairpin structure which is the receptor for the viral regulatory protein tat. Binding of the tat protein to TAR structure is an essential event in the virus life cycle. The TAR structure was used as an example to explore the different modes of pseudo-half-knot binding and the effects of inhibiting the binding of a known regulatory protein on gene expression in cells.

Figure 5:
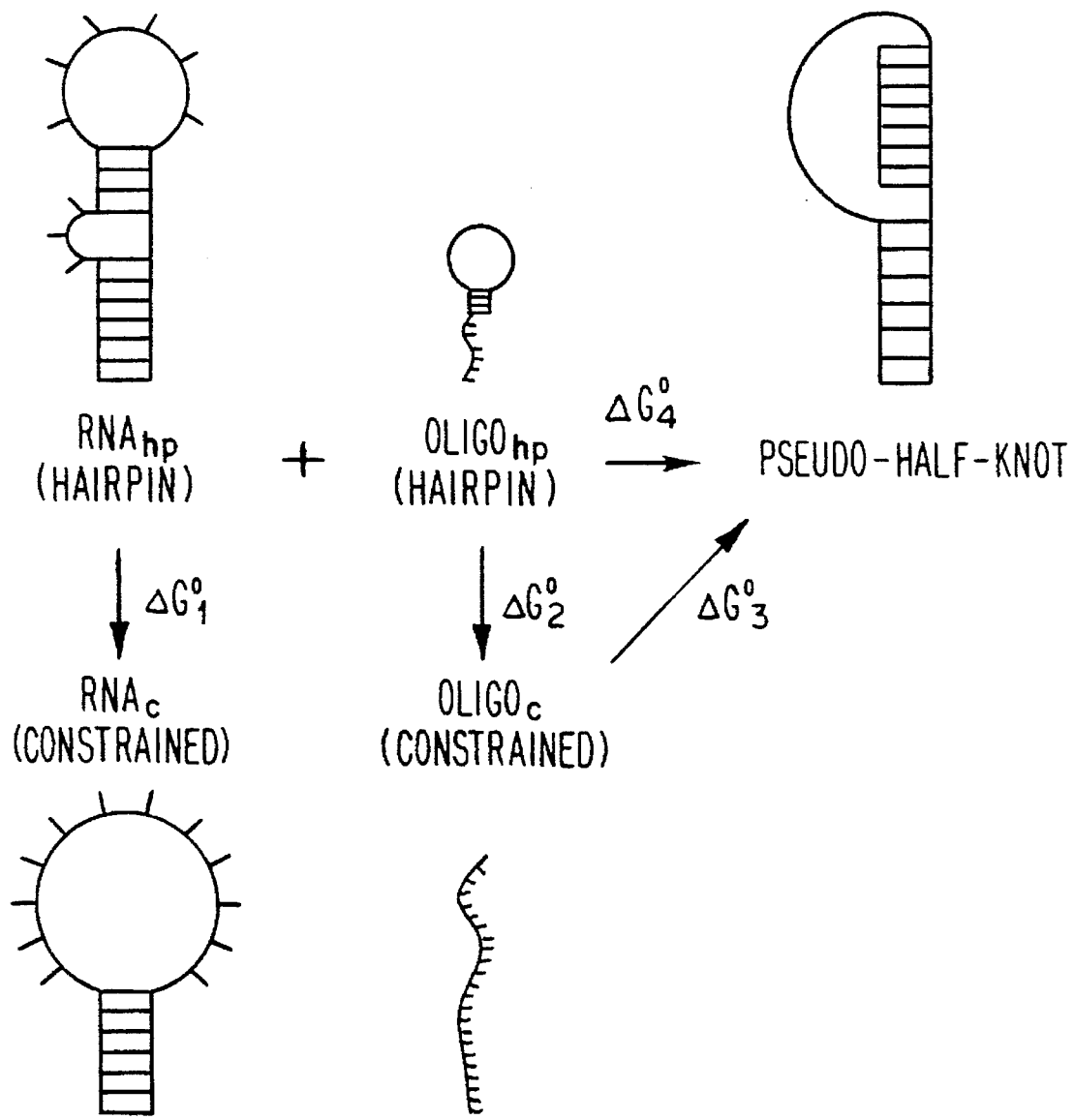
FIG. 5 shows a thermodynamic cycle describing the energetics of pseudo-half-knot formation with structural RNA. RNA folding rules were used to estimate $\Delta G°_1$, the free energy for disrupting the secondary structure of the target hairpin. The three-base bulge of the TAR element destabilizes the structure, so disrupting the first four base pairs of the TAR stem to form a 17-membered loop providing the largest number of bases available for binding with the lowest thermodynamic cost, only 5.2 kcal/mol. RNA folding rules were also used to estimate $\Delta G°_2$, the free energy required to unfold the oligonucleotide before binding to target. $\Delta G°_3$ refers to binding the unfolded oligonucleotide to the constrained hairpin loop. Three components contribute to $\Delta G°_3$: the new base pairs formed by the heteroduplex, $\Delta G°_{stem}$; the stack between the heteroduplex stem and the target stem, $\Delta G°_{stack}$; and the difference in loop penalties between the new pseudoknot loop and the previous RNA hairpin loop $\Delta\Delta G°_{loop}$. The $K_D$'s were measured experimentally by gel shift analysis and were reproducible within 5% between experiments.

Ideally, it is preferred to bind and disrupt regulatory protein binding sites by minimally perturbing the target structure elsewhere. Breaking base pairs in the target structure is thermodynamically unfavorable. However, in the case of TAR, the loop only contains six bases and the binding site for the tat protein includes a three base bulge and portions of the adjacent stems. The overall thermodynamics for pseudo-half-knot TAR binding can be estimated by using the thermodynamic cycle (FIG. 5). Although the free energy for disrupting the secondary structure cannot be measured directly, RNA folding rules, S. M. Freier, R. Kierzek, J. A. Jaeger, N. Sugimoto, M. H. Caruthers, T. Neilson, *Proc. Natl. Acad. Sci. U.S.A.* 83, 9373 (1986), can be used to estimate $\Delta G°_1$. The TAR element (FIG. 3) contains a 6 base loop and a 3 base bulge which destabilize the structure by 4.3 and 6.0 kcal/mol, respectively, which flank four base pairs which stabilize the structure by 9.1 kcal/mol. If the four base pairs were disrupted forming a 17 base loop, the overall thermodynamic cost is only 5.2 kcal/mol to create a loop with 17 continuous free bases for binding. Thus, disruption of the base pairs between the loop and bulge provides the largest number of bases available for binding with the lowest thermodynamic cost.

Secondary structure in the oligoribonucleotide, which also must be unfolded at a thermodynamic price ($\Delta G°_2$) before binding to target, must also be considered. This factor can be especially important when binding to stemloop targets. Complementary oligonucleotides symmetrically targeted around stemloop RNA's can form stemloops themselves. For oligoribonucleotides and close structural analogs, the RNA folding rules can also be used to estimate $\Delta G°_2$.

The most complex parameter to estimate is $\Delta G°_3$, for binding the oligonucleotide to the constrained hairpin loop to form a pseudo-half-knot. There are three components that contribute to $\Delta G°_3$; the new base pairs formed by the heteroduplex stem $\Delta G°_{stem}$, the stack between the heteroduplex stem and the target stem $\Delta G°_{stack}$, and the difference in loop penalties between the new pseudoknot loop and the previous RNA hairpin loop $\Delta\Delta G°_{loop}$. Thus, $\Delta G°_1$ is the thermodynamic parameter which is unfavorable to binding structured RNA, $\Delta G°_{stack}$ is a favorable contribution not available in typical antisense interactions, and $\Delta\Delta G°_{loop}$ can be favorable or unfavorable depending upon the size of the loop.

These parameters were estimated for three oligonucleotides targeted to the constrained TAR base loop using the Loop 1, Loop 2 and "all the way around (ATWA)" binding motifs (FIG. 4) and two oligonucleotides which disrupt three additional base pairs in the stem below the bulge. Calculations were compared with affinities measured experimentally by gel shift, and are shown in Table 1. RNA folding rules were used to estimate $\Delta G°_1$, the free energy for disrupting the secondary structure of the target hairpin. The three base bulge of the TAR element destabilizes the structure, so disrupting the first four base pairs of the TAR stem to form a 17-membered loop providing the largest number of bases available for binding with the lowest thermodynamic cost, only 5.2 kcal/mol. RNA folding rules were also used to estimate $\Delta G°_2$, the free energy required to unfold the oligonucleotide before binding to target. $\Delta G°_3$ refers to biding the unfolded oligonucleotide to the constrained hairpin loop. Three components contribute to $\Delta G°_3$: the new base pairs formed by the heteroduplex, $\Delta G°_{stem}$; the stack between the heteroduplex stem and the target stem, $\Delta G°_{stack}$; and the difference in loop penalties between the new pseudoknot loop and the previous RNA hairpin loop $\Delta\Delta G°_{loop}$. The $K_D$'s were measured experimentally by gel shift analysis and were reproducible within 5% between experiments.

TABLE 1

Thermodynamic calculations for pseudo-half-knotting TAR

| OLIGO | $\Delta G°_1$ | $\Delta G°_2$ | $\Delta G°_3$ | | | $\Delta G°_4$ # | $\Delta G°_4$ $ | $K_D$ nM |
| | | | $\Delta G°_{stem}$ | $\Delta G°_{CA-stack}$ | $\Delta\Delta G°_{loop}$ | calculated | observed | observed |
|---|---|---|---|---|---|---|---|---|
| L1-12 | 5.2 | 0.0 | −23.8 | −1.7 | +4.0 | −16.3 | −14.5 | 75 |
| L2-12 | 5.2 | 0.0 | −22.3 | −0.9 | +4.0 | −14.0 | −14.5 | 60 |
| ATWA-17 | 5.2 | 13.1 | −33.5 | — | +4.0 | −21.2 | −13.3 | 500 |
| L1-17 | 12.3 | 3.1 | −33.3 | −1.8 | +2.7 | −17.0 | −15.5 | 15 |
| L2-17 | 12.3 | 0 | −31.0 | −1.8 | +2.7 | −17.8 | −15.9 | 7 |

FOOTNOTES TO TABLE 1:
*Assumes all 17 bases of the loop are bound without disruption of the stem.
Calculations for 1 M NaCl.
$Observed values measured by gel shift in 100 nM NaCl.
All values are in kcal/mol. $\Delta G°_1$, $\Delta G°_2$, $\Delta G°_{stem}$, and $\Delta G°_{stack}$ were calculated using folding parameters for RNA. The $\Delta\Delta G°_{loop}$ is the difference between a pseudo-knot loop estimated at +10.4 kcal/mol. and the appropriate length hairpin loop.

The validity of these estimates depends upon the applicability of the RNA folding rules developed at 1M Na⁺ to physiological conditions. Agreement of the predicted and experimental values, as shown in Table 1, suggests that the rules are reasonably appropriate at least at lower ionic strengths. Both the Loop 1, 12-mer and Loop 2, 12-mer oligoribonucleotides had experimentally measured affinities close to the predictions.

Although the ATWA 17-mer oligonucleotide has more potential bases in the loop to bind, its measured affinity was an order of magnitude lower than either the Loop 1 or Loop 2 12-mers, which is consistent with the notion that binding "all the way around" is topologically impossible. Moreover, the ATWA 17-mer oligonucleotide has significant internal structure ($\Delta G°_2$) which is unfavorable to binding. However, if the 17-mer oligonucleotides are targeted to TAR in a fashion which creates a pseudo-half-knot (L1-17 and L2-17), binding affinity increased by two orders of magnitude. The 17-mer pseudo-halfknot oligonucleotides are calculated to bind TAR with greater affinity than the 12-mers. However, this is not directly due to an increased number of base pairs formed between the oligonucleotide and the target. Longer is not necessarily better, because the affinity gained from increasing the number of bases bound to the target ($\Delta G°_{stem}$) is compensated by the unfavorable disruption of base pairs in the target ($\Delta G°_1$).

Whether this is a net gain or loss depends upon which near neighbor pairs become part of the heteroduplex, the $\Delta\Delta G°_{loop}$ difference due to loop lengths, and whether more internal structure is created in the oligonucleotide because it is longer. The observed binding affinities of the pseudo-half-knot 17-mer oligonucleotides were higher than the 12-mers by an order of magnitude and in rank order agreement with the predicted affinities, as shown in Table 1. Discrepancies in the absolute values may derive from the lack of certainty in the loop penalties and the differences between the predicted values calculated for 1M Na⁺ and the measurements at physiological salt concentrations.

Both the binding affinity per base pair and the structure of the helix formed are important considerations in pseudo-half-knot binding strategies. Near neighbor hybridization parameters are only available for RNA-RNA or DNA-DNA, K. J. Breslauer, R. Frank, H. Blocker, L. A. Marky, *Proc. Natl. Acad. Sci. U.S.A.* 83, 3746 (1986), but not RNADNA heteroduplexes. RNA-RNA heteroduplexes form an A-type helix, W. Saenger, *Principles of Nucleic Acid Structure* (Springer-Verlag, New York, 1983), which was used as the structural model for all topological measurements. 2'-O-methyl oligonucleotides are close structural analogs of RNA which have nearly identical hybridization affinities, form A-type duplex structures when bound to RNA, and are resistant to nucleolytic degradation, B. S. Sproat, A. I. Lamond, B. Beijer, P. Neuner, U. Ryder, *Nucleic. Acids. Res.* 17, 3373 (1989). Gel shift experiments comparing 2'-O-methyl oligonucleotides and oligoribonucleotides for TAR binding showed only small differences. Structure mapping experiments as described below also could not distinguish 2'-O-methyl oligonucleotides and oligoribonucleotides.

In contrast, both DNA oligonucleotides and phosphorothioate DNA oligonucleotides showed no detectable binding for the Loop 1 and Loop 2, 12-mer oligonucleotides, and very weak binding for the Loop 1 and Loop 2, 17-mer oligonucleotides. 2'-O-methyl phosphorothioate oligonucleotides bound TAR in with approximately ten fold lower affinities than 2'-O-methyl phosphodiesters. See Table 2.

TABLE 2

Effect of chemical composition and loop structure on KD's for oligonucleotide binding to TAR RNA.

| ANTISENSE OLIGONUCLEOTIDE (TARGET SITE) | COMPOSITION | TAR BINDING $K_D$ (nM) |
|---|---|---|
| L1-12 (28–39) | RNA | 75 |
| | DNA | >100 μM |
| | P=S | >100 μM |
| | O—Me | 70 |
| 12-12 (23–34) | RNA | 60 |
| | O—Me | 30 |
| ATWA-17 (23–39) | RNA | 500 |
| L1-17 (26–42) | RNA | 25 |
| | DNA | >100 μM |
| | O—Me | 18 |
| | P=S, O—Me | 200 |
| L2-17 (20–36) | RNA | 15 |
| | DNA | >100 μM |
| | O—Me | 7 |
| | P=S, O—Me | 150 |

Figures 3A, 3B, 3C, 3D:
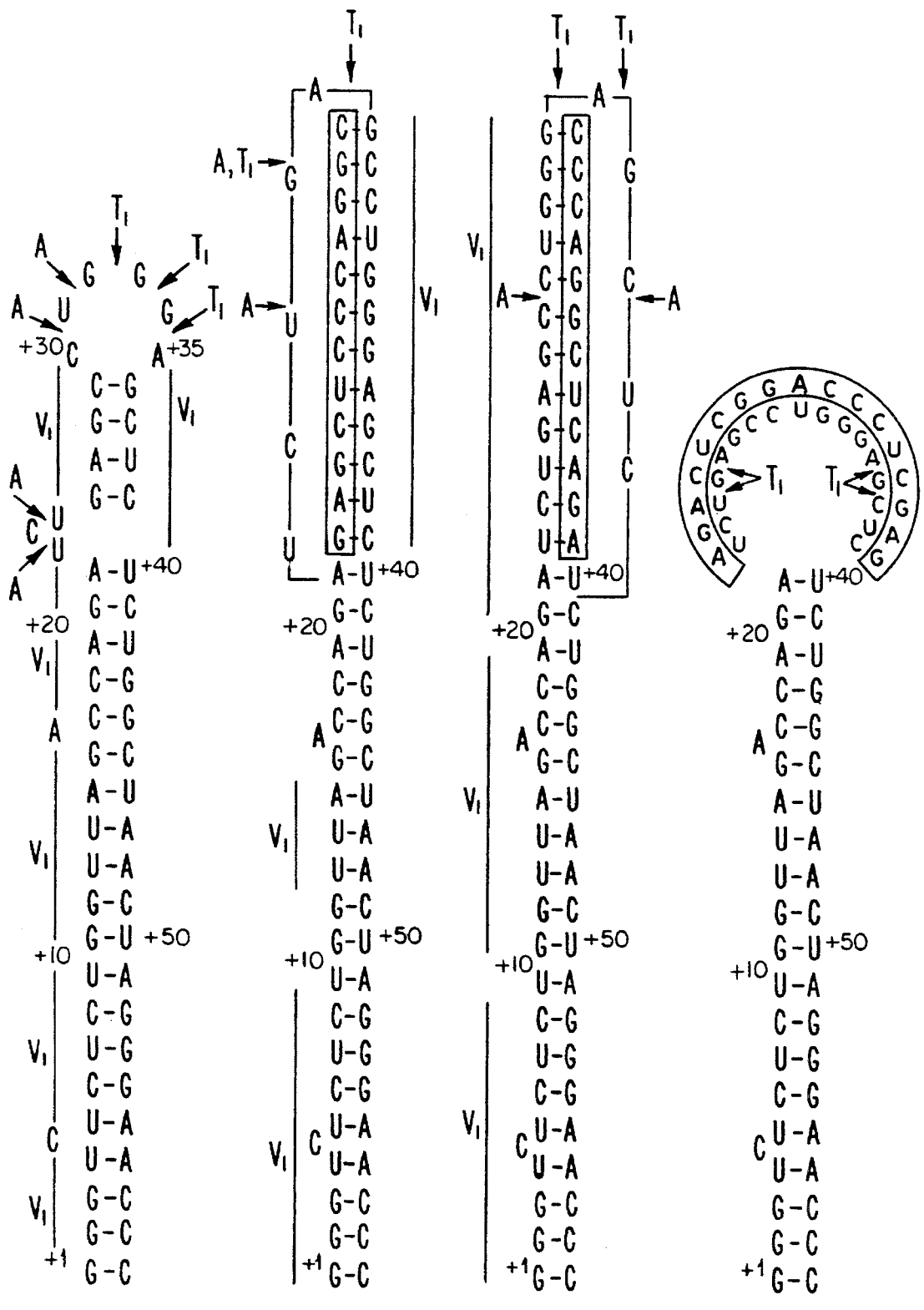
FIG. 3 comprising parts A–D shows sites of nuclease sensitivity in pseudo-half-knotted TAR RNA. 100 pM TAR (A) was hybridized with 100 nM Loop 1, 12-mer oligonucleotide (B), 100 nM Loop 2, 12-mer oligonucleotide (C), 1 mM "all the way around" (ATWA) (D) or no oligonucleotide for 30 minutes at 37° C. in 50 mM NaCl, 5 mM MgCl2, 10 mM Tris, pH 7.4, followed by incubation with nuclease. RNAse T1 and A cleave, respectively, at single stranded G's or pyrimidines; RNAse V1 cleaves double stranded regions. Only the T1 cleavages are shown on the ATWA complex.

Binding was done in 100 mM NaCl with 5'end labeled TAR and analyzed by gel shift. The target site numbering for TAR is indicated in FIG. 3A.

Pseudo-half-knot structure determination

The structures of five hybrid complexes were characterized using enzyme and chemical probes. Both the pseudo-half-knot 12-mer oligonucleotides shown in FIG. 3 and the 17-mer oligonucleotides showed cleavage patterns consistent with the predicted structures. The loop and bulge regions of TAR, which were sensitive to the single strand specific nucleases RNAse A and RNAse T1 became protected upon pseudo-half-knot oligonucleotide binding. New, previously uncleaved positions corresponding to predicted single stranded regions in the pseudo-half-knot became sensitive. Similarly, the double stranded regions in TAR were sensitive to the double strand specific RNAse V1. After oligonucleotide binding the new V1 cleavage patterns correlated with the predicted pseudo-half-knot structure. The integrity of the stem region below the bulge was maintained in all cases as determined by the V1 pattern, as shown in FIG. 3.

The ATWA-17-mer oligonucleotide cleavage pattern was also consistent with a pseudo-half-knot structure with only 12 of the 17 possible base pairs formed and the unbound fragment of oligonucleotide dangling from the structure. There was no evidence from the V1 cleavage pattern that the stem was disrupted below the bulge. Although the ATWA-17-mer has a choice of binding via the Loop 1 or Loop 2 motifs, the cleavage pattern suggests that the ATWA-17-mer oligonucleotide bound HIV TAR to form a mixed population of Loop 1 and Loop 2 pseudo-half-knots. This is consistent with the observation that the Loop 1 and Loop 2 12-mer oligonucleotides have nearly identical affinities for TAR.

Functionality placement in a pseudo-half-knot

Figure 6A:
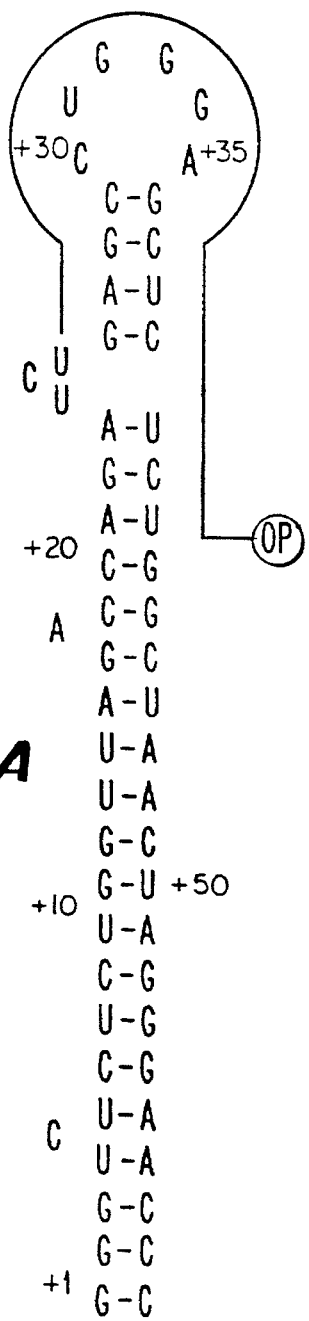
FIG. 6 comprising A–C shows that TAR can be cleaved by tethering an appropriate cleavage moiety on the pseudo-half-knot oligonucleotide.
Figure 6B:
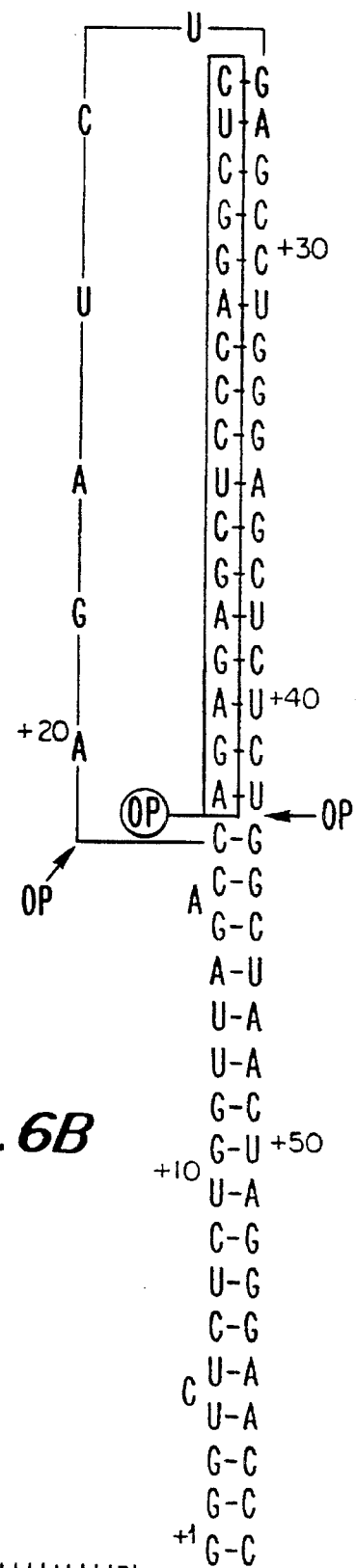
Figure 6C:
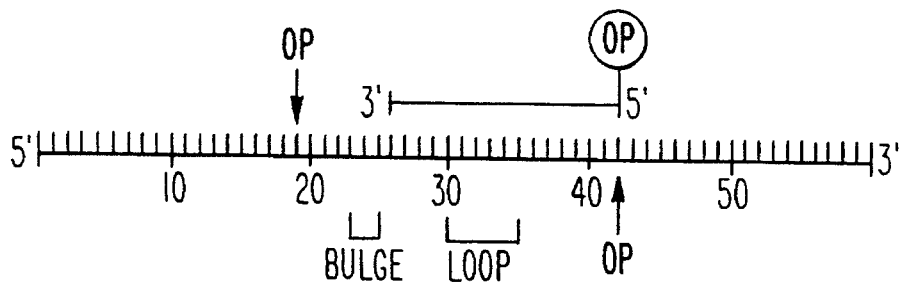

The structure of the Loop 1, 17-mer pseudo-half-knot was further characterized by the cleavage pattern obtained from an orthophenanthroline (OP) tethered oligonucleotide. OP-oligonucleotides have been shown to cleave RNA and in the presence of copper and reducing agents, at sites close to the OP, D. S. Sigman, *Acc. Chem. Res.* 19, 180 (1986). OP was tethered to the 5'-end of the L1-17-mer oligonucleotide on the 5' position on the ribose using a thiol linker, C.B. Chen, D. S. Sigman, *J. Am. Chem. Soc.* 110, 6570 (1992) (FIG. 6). No difference in binding affinity between the OP-L1-17-mer and the untethered L1-17-mer was observed by gel shift analysis, and no change was observed in the enzyme mapping pattern, suggesting that the tethered OP moiety does not perturb the L1-17 pseudo-half-knot structure.

Molecular models of the L1-17 pseudo-half-knot structure place the OP in the major groove at the three strand junction of the L1-17 pseudo-half-knot. Upon addition of reducing agent to initiate OP cleavage, two predominant cuts in the HIV TAR are observed at C-19 and U-42.

There are two possible paths for the L1-17 loop to return to the top of the structure which are difficult to distinguish experimentally. One path is to follow the major groove as shown in FIG. 2B. This is the only topologically available route for shorter pseudoknot Loop 1's. The other path is to "flip out" of the helix as shown in FIG. 2C. Molecular modeling shows that the flip-out path is shorter because the 17 base stem and periodicity of the helix places the connection sites on the same face of the double helix (FIG. 2C). The flip-out path also seems more likely because there is less unfavorable phosphate crowding outside the helix than in the major groove. The experimental results showed that the OP moiety tethered into the major groove did not affect the binding affinity or structure of the L1-17 complex. Moreover, RNAse T1 strongly cleaved G-21 in the L1-17 complex which may have been obscured if the loop were inside the major groove.

A key advantage to binding RNA in the pseudo-half-knot motif is the potential to direct reactive moieties to single stranded loop regions of the target RNA. Cleavage reagents are particularly useful, as indicated by the OP example.

Optical melts

Another tool to probe pseudo-half-knot structures is optical melts. Absorbance vs. temperature measurements for TAR RNA showed a strong absorbance transition at 70° C. suggesting a two state folded and unfolded model. In contrast, the L1-17 and L2-17 pseudo-half-knot structures showed two transitions at 70° C. and 82° C. Optical melts of the L1-17 and L2-17 oligonucleotides against complementary unstructured RNA showed transitions at approximately 80° C. The optical melt data is consistent with the chemical and enzymatic cleavage model for a highly structured complex which melts first by an intramolecular unfolding of the TAR lower stem structure, followed by a higher temperature dissociation of the oligonucleotide. The 70° C. melting transition for all three structures suggests that the pseudo-half-knots do not contribute to the cooperativity stabilizing the lower stem.

Disruption of tat peptide binding

Pseudo-half-knot formation disrupts the natural structure of TAR in the region specifically recognized by the tat protein. Peptide fragments of tat which contain the TAR-binding domain have been shown to specifically bind to the bulge region of TAR with about a five-fold greater affinity than second and third binding sites on TAR, K. M. Weeks, C. Ampe, S. C. Schultz, T. A. Steitz, D. M. Crothers, Science 249, 1281 (1990). A 25 amino acid tat fragment (from 48–72 in the tat protein sequence, tat25), when bound to the TAR element in 1:1 stoichiometry, specifically protected the bulge region from enzymatic cleavage by RNAase A. On a native acrylamide gel the 1:1 tat25:TAR complex migrated at a location distinct from both uncompeted TAR and TAR bound in a pseudo-half-knot.

Figure 4:
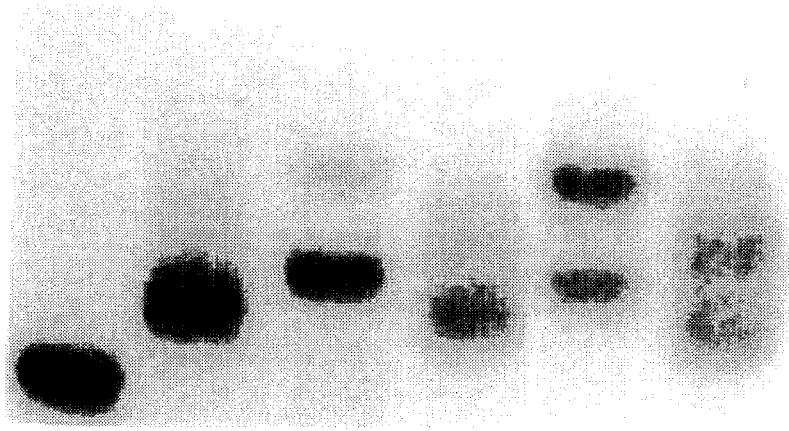
FIG. 4 shows the results of gel mobility shift assays. Inhibition of HIV tat peptide binding by pseudo-halfknot oligonucleotides is shown.

To determine if the oligonucleotides could compete with tat25 for TAR, a prebound 1:1 tat25:TAR complex was incubated with the Loop 1-forming oligonucleotide 12-mer at 500 nM. Gel shift experiments showed that the oligonucleotide completely displaced the tat peptide from TAR (FIG. 4, fourth lane) and formed a pseudo-half-knot. At higher concentrations of peptide, second site (non-bulge site) binding occurred as expected and the pseudo-half-knot complex was shifted to a higher location on the gel (FIG. 4, sixth lane). The temporal order of addition of either the antisense oligonucleotide or tat25 had no effect on the nature or concentration dependence of complexes formed after an initial 30 min incubation. Identical results were obtained with the Loop 2-forming 12-mer. Random control oligomers had no effect on titrations of TAR with either tat25 or antisense compounds.

These results further confirm that L1-12 and L2-12 bind and disrupt the tat binding site on TAR and that the oligonucleotides are able to bind the preformed 1:1 tat25-TAR complex, probably through initial hybridization at the loop with subsequent branch migration to disrupt the bulge structure and displace the peptide.

Inhibition of TAR/tat transactivation in cell culture

The molecular events in HIV TAR/tat transactivation have been widely studied by co-transfecting a plasmid which contains the HIV long terminal repeat (LTR) fused to an easily assayable reporter gens and a plasmid which expresses tat protein into cells, C. Dingwall, I. Ernberg, M. J. Gait, et al, EMBO J. 9, 4145 (1990); S. Roy, U. Delling, C.-H. Chen, C. A. Rosen, N. Sonenberg, Genes Dev. 4, 1365 (1990); C. A. Rosen, G. N. Pavlakis, AIDS 4,499 (1990); M.-C. Hsu, A. D. Schutt, M. Holly, et al, Science 254, 1799 (1991). Tat protein produced from the latter plasmid will bind to the TAR element and enhance gens expression from the HIV LTR by over 100 fold, as measured by assaying the reporter. We have constructed an HIV LTR luciferass plasmid and used the co-transfection method to test whether the pseudo-half-knot oligonucleotides can specifically inhibit tat/TAR transactivation in the cell.

Figure 7:
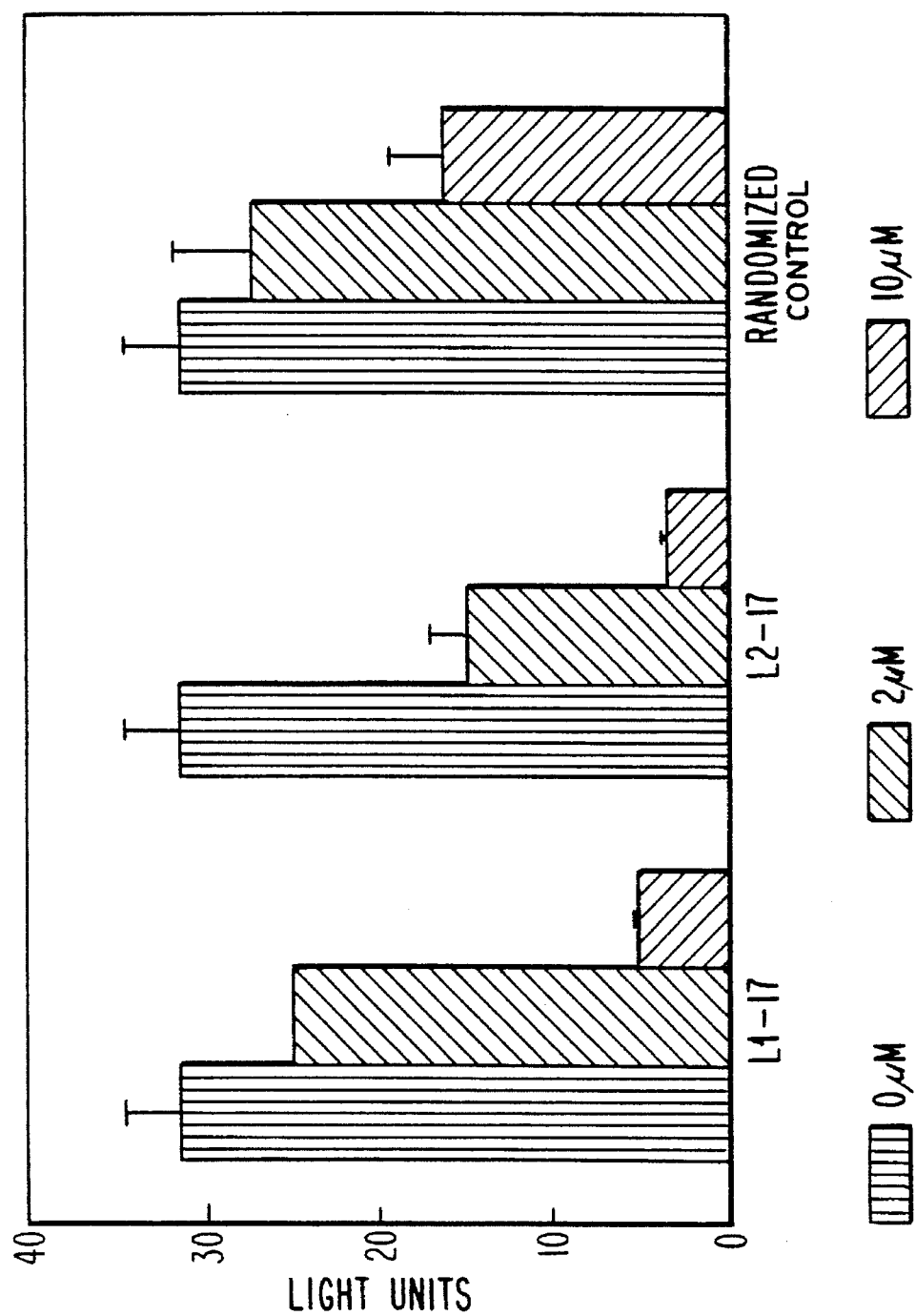
FIG. 7 shows inhibition of HIV gene expression by a pseudo-half-knot forming oligonucleotide (B). Inhibition of gene expression was measured as described in Vickers et al., *Nuc Acids Res* 19(12):3359–3368 (1991), except that luciferase was used as a reporter gene instead of alkaline phosphatase. The oligonucleotides used in the experiment were 2'-O-methyl 17 mers, as indicated in Table 2. Cells were pre-treated with oligonucleotides for 3 hours, transfected with plasmids and then post-treated at the indicated concentrations. The control oligonucleotide was composition and length matched to L1-12, but with the sequence randomized.

When 2'-O-methyl L1-17 and L2-17-mer oligonucleotides are co-transfected into cells with the plasmids, both compounds inhibited transactivation in a sequence dependent manner (FIG. 7).

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotide.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following examples illustrate the present invention and are not intended to limit the same.

EXAMPLES

Example 1

Inhibition of tat peptide by pseudo-half-knot oligonucleotides

To determine if the oligonucleotides could compete with tat25 for TAR, 32P labelled TAR was incubated with tat25 and/or the L1-12 oligonucleotide. At peptide concentrations where the 1:1 tat25: TAR complex predominates, the oligonucleotide completely displaced the tat peptide (FIG. 4, lane 4). At higher peptide concentrations, second (non-bulge) site binding occurred and the pseudo-half-knot complex was shifted to a higher location on the gel (FIG. 4, lane 6) with the oligonucleotide remaining attached. Identical results were obtained with the L2-12-mer and were independent of the order of addition.

N-acetylated tat25 used was obtained from the UCSF Biotechnology Resource Core facility. Gel mobility shift assays were performed by the addition of 5'-P32-TAR RNA and Tat25 at 500 nM and 0.02 and 12.5 nM concentrations, respectively, to a 10 µl reaction containing 10 mM tris-HCl pH 7.5, 70 mM NaCl, 0.2 mM EDTA, 5% (v/v) glycerol, 500 nM BSA, and 40 ng pdIdC. Each binding mix was incubated for 30 minutes at 4° C. and then loaded directly onto a 15% native PAGE. The results are shown in FIG. 4.

What is claimed is:

1. A method for preparing an oligonucleotide having at least 12 contiguous nucleotide units capable of binding to a selected RNA having at least one stem-loop structure comprising:

a) selecting an oligonucleotide sequence having at least 12 contiguous nucleotide units complementary to the loop portion of either the 3' or 5' side of said stem-loop structure;

b) determining the ability of the selected oligonucleotide to form a pseudo-half-knot with said stem-loop structure; and c) if the selected oligonucleotide is determined to be capable of forming a pseudo-half-knot with said stem-loop structure, synthesizing the selected oligonucleotide.

2. The method of claim 1 wherein said selected oligonucleotide has a reactive moiety tethered at its 5' end, its 3' end, a 2' position on a sugar, a phosphate, or a heterocycle ring.

3. The method of claim 1 wherein a plurality of oligonucleotides are prepared.

4. The method of claim 1 wherein a plurality of oligonucleotides are selected which are complementary to the loop portions of either the 3' or 5' side of said stem-loop structure, determinations of the ability of each of said plurality to form a pseudo-half-knot with said stem-loop structure are made, and the oligonucleotide is synthesized having the greatest ability to form said pseudo-half-knot structure.

5. The method of claim 1 wherein the stem-loop structure is the HIV TAR element or rev responsive element.

6. A method for preparing an oligonucleotide having at least 12 contiguous nucleotide units capable of binding to a selected RNA having at least one stem-loop structure comprising:

a) selecting an oligonucleotide sequence having at least 12 contiguous nucleotide units complementary to the loop portion of either the 3' or 5' side of said stem-loop structure said selecting comprising predicting by RNA folding rules whether said RNA sequence is capable of forming a pseudo-half-knot with the selected RNA; and b) synthesizing an oligonucleotide having said sequence.

7. A method for obtaining an oligonucleotide having a sequence of at least 12 contiguous nucleotide units capable of binding to a selected RNA having at least one stem-loop structure comprising:

a) selecting an oligonucleotide having a sequence of at least 12 contiguous nucleotide units complementary to the loop portion of either the 3' or 5' side of said stem-loop structure; and b) obtaining a complementary oligonucleotide predicted by RNA folding rules to be capable of forming a pseudo-half-knot with the selected RNA so that when said oligonucleotide binds to said selected RNA at the stem-loop structure.

8. A method for modulating expression of a selected RNA in vitro having at least one stem-loop structure comprising:

a) selecting an oligonucleotide sequence complementary to the loop portion of either the 3' or 5' side of said stem-loop structure said oligonucleotide having at least 12 contiguous nucleotide units;

b) determining the ability of the selected oligonucleotide to form a pseudo-half-knot with said stem loop structure; and c) if the selected oligonucleotide is determined to be capable of forming a pseudo-half-knot with said stem-loop structure, contacting the RNA with the selected oligonucleotide, thereby modulating expression of said selected RNA.

9. A method for modulating expression of a selected RNA in vitro having at least one stem-loop structure comprising:

a) selecting an oligonucleotide sequence complementary to the loop portion of either the 3' or 5' side of said stem-loop structure and predicted by RNA folding rules to be capable of forming a pseudo-half-knot with the selected RNA said oligonucleotide having at least 12 contiguous nucleotide units; and b) contacting the oligonucleotide with the RNA, thereby modulating expression of said selected RNA.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 57
        ( B ) TYPE: Nucleic Acid
        ( C ) STRANDEDNESS: single
        ( D ) TOPOLOGY: linear ( i v ) ANTI-SENSE:

( x i ) SEQUENCE DESCRIPTION: SEQ ID NO: 1:

GGGUUCUCUG GUUAGCCAGA UCUGAGCCUG GGAGCUCUCU GGCUAACUAG          5 0

GGAACCC          5 7

( 2 ) INFORMATION FOR SEQ ID NO: 2:

( i ) SEQUENCE CHARACTERISTICS:
        ( A ) LENGTH: 66
        ( B ) TYPE: Nucleic Acid
        ( C ) STRANDEDNESS: single
        ( D ) TOPOLOGY: linear ( i v ) ANTI-SENSE:

( x i ) SEQUENCE DESCRIPTION: SEQ ID NO: 2:

GGGUCUCUCU GGUUAGCCAG AGAGCUCCCA GGCGGGUCUC UCUGGUUAGC          5 0

CAGAUCUGAG CCUGGG          6 6

( 2 ) INFORMATION FOR SEQ ID NO: 3:

( i ) SEQUENCE CHARACTERISTICS:
        ( A ) LENGTH: 59
        ( B ) TYPE: Nucleic Acid
        ( C ) STRANDEDNESS: single
        ( D ) TOPOLOGY: linear ( i v ) ANTI-SENSE:

( x i ) SEQUENCE DESCRIPTION: SEQ ID NO: 3:

GGGUCUCUCU GGUUAGACCA GAUCUGAGCC UGGGAGCUCU CUGGCUAACU          5 0

AGGGAACCC          5 9

( 2 ) INFORMATION FOR SEQ ID NO: 4:

( i ) SEQUENCE CHARACTERISTICS:
        ( A ) LENGTH: 17
        ( B ) TYPE: Nucleic Acid
        ( C ) STRANDEDNESS: single
        ( D ) TOPOLOGY: linear ( i v ) ANTI-SENSE:

( x i ) SEQUENCE DESCRIPTION: SEQ ID NO: 4:

AGACUCGGAC CCUCGAG                      17

( 2 ) INFORMATION FOR SEQ ID NO: 5:

( i ) SEQUENCE CHARACTERISTICS:
        ( A ) LENGTH: 12
        ( B ) TYPE: Nucleic Acid
        ( C ) STRANDEDNESS: single
        ( D ) TOPOLOGY: linear ( i v ) ANTI-SENSE:

( x i ) SEQUENCE DESCRIPTION: SEQ ID NO: 5:

GAGCUCCCAG GC                          12

( 2 ) INFORMATION FOR SEQ ID NO: 6:

( i ) SEQUENCE CHARACTERISTICS:
        ( A ) LENGTH: 12
        ( B ) TYPE: Nucleic Acid
        ( C ) STRANDEDNESS: single
        ( D ) TOPOLOGY: linear ( i v ) ANTI-SENSE:

( x i ) SEQUENCE DESCRIPTION: SEQ ID NO: 6:

AGACUCGGAC CG                          12